Figure 1:
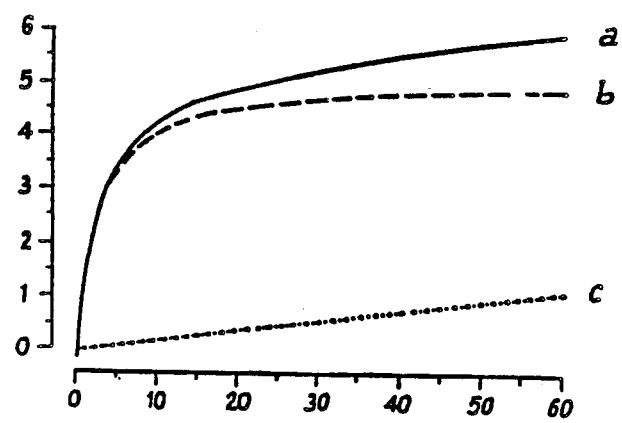

United States Patent [19]

Shroot et al.

[11] Patent Number: 4,880,941
[45] Date of Patent: Nov. 14, 1989

[54] TRITIUM LABELLED COMPOUND, ITS PREPARATION AND ITS USE IN THE DETERMINATION OF THE AFFINITY OF RETINOIDS FOR THEIR CELLULAR RECEPTOR

[75] Inventors: Braham Shroot, Antibes; Oliver Watts, Cagnes sur Mer; Joseph Gazith, Biot; Marie-Thérèse Cavey, Valbonne, all of France

[73] Assignee: Centre International de Recherches Dermatologique (CIRD), Valbonne, France

[21] Appl. No.: 90,324

[22] Filed: Aug. 28, 1987

[30] Foreign Application Priority Data

Aug. 29, 1986 [FR] France .................................. 86 12237

[51] Int. Cl.[4] ........................................... C07D 333/54
[52] U.S. Cl. ...................................................... 549/57
[58] Field of Search ........................................... 549/57

[56] References Cited

PUBLICATIONS

Chem. Abstracts 107:3960f *Preparation of Benzofurans and their Analogs for Treatment of Skin Ailments*, Shroot, Braham; Eustache, Jacques; Jean Michelle Bernardon, Sep. 19, 1984.

*Primary Examiner*—Mary C. Lee
*Assistant Examiner*—F. Brenda Magrab
*Attorney, Agent, or Firm*—Cushman, Darby & Cushman

[57] ABSTRACT

2-(5,6,7,8-Tetrahydro-5,5,8,8-tetramethyl-2-naphthyl)-6-benzo [b] thiophene carboxylic acid labelled with tritium, its preparation and its use as a radioactive marker in the determination of the affinity of, the presence of, or the amount of, retinoids having a carboxylic group and/or in the characterization of antibodies directed against this acid and/or in the quantification of the cRABP receptor of said retinoids.

4 Claims, 4 Drawing Sheets

TRITIUM LABELLED COMPOUND, ITS PREPARATION AND ITS USE IN THE DETERMINATION OF THE AFFINITY OF RETINOIDS FOR THEIR CELLULAR RECEPTOR

The present invention relates to a retinoid related compound labelled with tritium, to its preparation and to its use principally in the determination of the affinity of retinoids for their cellular receptor and/or the determination of the cellular amount in the corresponding receptor.

It is known that retinoids constitute a recognized class of compounds which act principally on the proliferation and differentiation of numerous types of cells; see for example B. A. Pawson and Coll., Journal of Medicinal Chemistry, Vol. 25, No. 11, pages 1269–1277 (1982).

Retinoids have been used particularly in the treatment of various dermatologic disorders in which a maladjustment of the control mechanisms of proliferation and differentiation of the epidermic cells is implied; see for example the work "Update: Dermatology in General Medicine", edited by Thomas B. Fitzpatrick et al, McGraw-Hill Book Company, published in 1983, and in particular the chapter by D. B. Windhorst et al, entitled, "The Retinoids", pages 226–237.

The mode of action of retinoids is still not well known. It has been shown, however, that there exists in the cells a receptor called cRABP (cellular Retinoic Acid-Binding Protein) which is specific for retinoids having an acid group.

The determination of the affinity constant (Kd) for cRABP, of a retinoid having an acid group, constitutes a particularly quick means for evaluating the potential biologic activity of said retinoid.

Several experimental methods permit the determination of the affinity constant of a ligand for its receptor. A direct method, in particular, can be employed if the ligand under consideration is radioactively labelled, or by competition with a radioactive ligand if the ligand under consideration is not radioactively labelled.

A good radioactive ligand must, on the one hand, have a high affinity for its receptor and, on the other hand, have a weak fixation on any other molecule. Besides, it must be sufficiently stable so as to be used in a convenient or commodius manner.

In the case of retinoid acids, the radioactive ligand generally used is most often retinoic acid tritiated, either in position 2 (J. Labelled Compounds and Radiopharmaceuticals XVIII, p. 1099, (1980), or in position 4 (German patent application No. 3.142.975).

While retinoic acid certainly exhibits excellent affinity for cRABP, with a weak nonspecific fixation, it nonetheless exhibits the disadvantage of rapidly degrading, by radiolysis, oxidation and photolysis.

It has now been discovered that tritiated 2-(5,6,7,8-tetrahydro-5,5,8,8-tetramethyl-2-naphthyl)-6-benzo [b]thiopene carboxylic acid constitutes a new radioactive ligand which exhibits an excellent affinity for cRABP and a weak nonspecific fixation character. Moreover, this new ligand is very stable and can be obtained with a high specific activity which makes it particularly useful for the measurement of the affinity of retinoids for cRABP.

The present invention thus relates to 2-(5,6,7,8-tetrahydro-5,5,8,8-tetramethyl-2-naphthyl)-6-benzo [b]thiophene carb oxylic acid labelled with tritium and in particular to this acid whose methylidyne group in position 3 of the tetrahydronaphthalene group is labelled with tritium. The compound of the present invention can be provided alone or in admixture with the unlabelled acid.

The present invention relates principally to a new radioactive ligand, such as defined above, having a specific activity greater than 1 Ci/mmole and preferably at least equal to 2 Ci/mmole, or about 75 GBq/mmole.

The present invention also relates to a process for preparing the new radioactive ligand, such as defined above. This process involves known procedures for labelling chemical compounds with tritium such as those analogous to the process disclosed in the Journal of Labelled Compounds And Radiopharmaceuticals", Vol. XXII, pp. 843–850, 1985.

More specifically, the process of the present invention comprises preparing 2-(3-halogeno-5,6,7,8-tetrahydro-5,5,8,8-tetramethyl-2-naphthyl)-6-benzo [b] thiophene carboxylic acid and submitting this acid to the action of a tritiated reducing agent.

The reducing agent is, for example, tritiated hydrogen which is used in the presence of an appropriate catalyst, principally a palladium-based catalyst.

The reduction of the 3-halogen derivative is carried out preferably at ambient temperature and pressure, for example, at 15°–30° C. under a pressure of 1 bur (or about $10^5$ Pa).

The halogenated derivative employed, as a starting material, is preferably a brominated derivative.

2-(3-halogeno-5,6,7,8-tetrahydro-5,5,8,8-tetramethyl-2-naphthyl)-6-benzo [b] thiophene carboxylic acid can itself be prepared by reacting 2-(5,6,7,8-tetrahydro-5,5,8,8-tetramethyl-2-naphthyl)-6-benzo [b] thiophene carboxylic acid with a halogenation agent, in particular, a bromination agent. For example, the brominated derivative can be obtained by reacting the aforesaid acid with a bromination agent, such as N-bromo succinimide in dimethyl formamide, at a reaction temperature ranging from 0° to 50° C. and preferably from 0° to 20° C.

2-(5,6,7,8-tetrahydro-5,5,8,8-tetramethyl-2-naphthyl)-6-benzo [b] thiophene carboxylic acid (hereinafter designated as compound A) is a known product and can be obtained in accordance with the procedure described, for example, in French patent application No. 85.13747 (2,570,377) filed Sept. 17, 1985.

The present invention also relates to an intermediate product which is obtained in the process described above, i.e. 2-(3-halogeno-5,6,7,8-tetrahydro-5,5,8,8-tetramethyl-2-naphthyl)-6-benzo [b] thiophene carboxylic acid, and in particular to the brominated derivative thereof.

The radioactive ligand of the present invention can also be obtained starting with 2-(5,6,7,8-tetrahydro-5,5,8,8-tetramethyl-2-naphthyl)-6-benzo [b] thiophene carboxylic acid by isotopic exchange with tritiated water in the presence of platinum and acetic acid at a temperature ranging from, preferably, 20 to 150° C. In this case, the isotopic exchange is made, preferably, with the aromatic protons of the ligand.

The present invention also relates to the use of tritiated 2-(5,6,7,8-tetrahydro-5,5,8,8-tetramethyl-2-naphthyl)-6-benzo [b]thiophene carboxylic acid, which is tritiated, in particular, in position 3 of the tetrahydronaphthalene group, as a radioactive marker principally in the determination of the affinity of, the presence of, or the amount of, retinoids having a carboxylic group and/or in the quantification of the cRABP receptor of said retinoids.

For example, the radioactive marker of the present invention can be employed during the purification of the cRABP receptor by known exclusion or ion exchange chromatography methods under low or high pressure: it is sufficient to add to the tissular extract, used as a starting material, a determined amount of the radioactive ligand. The cRABP receptor thus finds itself labelled and its presence or absence in a given fraction can be easily registered.

The knowledge of the fixation curves on the receptor also permits the use of the marker of the present invention in the quantification of the receptor.

The radioactive marker of the present invention can also be employed in the characterization of antibodies against compound A, these antibodies (obtained in accordance with known methods of antihapten antibodies) being themselves useful in the determination of product A, fixed or not, on its receptor.

The radioactive marker of the present invention can also be employed in the study of intracellular activity mechanism and general metabolism of compound A.

The following nonlimiting examples illustrate the present invention.

Example 1 -
2-(3-$^3$H-5,6,7,8-tetrahydro-5,5,8,8-tetramethyl-2-naphthyl)-6-benzo [b] thiophene carboxylic acid (a) A mixture of said nontritiated acid (500 mg; 1.37 mmole) and N-bromosuccinimide (302 mg; 1.70 mmole) in 15 ml of DMF is stirred at ambient temperature for 24 hours, under a nitrogen atmosphere. The resulting mixture is added to 30 ml of 1N HCl and the product is extracted with ethyl ether (130 ml). The ether phase is separated, washed with water, dried on anhydrous magnesium sulfate, and the solvents are evaporated under reduced pressure. A pale brown solid is obtained which is then recrystallzied twice in a 50:50 isooctane/tetrahydrofuran mixture to obtain 380 mg (63% yield) of 2-(3-bromo-5,6,7,8-tetrahydro-5,5,8,8-tetramethyl-2-naphthyl)-6-benzo [b] thiophene carboxylic acid which melts at 272°-275° C.

| Elemental analysis | C | H | Br | O | S |
|---|---|---|---|---|---|
| Calculated | 62.30 | 5.23 | 18.02 | 7.22 | 7.23 |
| Found | 62.49 | 5.06 | 17.94 | 7.44 | 7.77 |

The position of the bromine atom is confirmed by analysis of the NMR proton spectrum of the above compound, and comparison with the NMR spectrum of the nonbrominated product.

(b) The resulting brominated compound (25 mg; 0.05 mmole) is dissolved in 2 ml of dry dioxan; 10 mg of palladium on carbon (10%) and 20 microliters (0.14 mmole) of triethylamine are added. The resulting mixture is stirred at ambient temperature, under a tritium atmosphere (pressure about 1 bar), for 20 hours. The catalyst is removed by filtration and the solvents are evaporated under a vacuum.

The residue is dissolved in a mixture of methanol and ethyl acetate and the solvents are then evaporated under reduced pressure. This procedure is repeated twice. The resulting residue is then dissolved in a minimum of tetrahydrofuran and purified by preparative plate chromatography (0.2×20×20 cm silica plate; eluant - 9:1 dichloromethane/methanol mixture). The bond fluorescing under UV irradiation at 366 nm is recovered.

The final product is dissolved in 10 ml of methanol. Its purity is verified by thin layer chromatography (silica plate and eluant as described above). A single spot is apparent under UV irradiation (254 and 366 nm) and during beta counting. By HPLC (inverse phase, Zorbax ODS column, eluant: 95/5 mixture of acetonitrile/0.02% acetic acid solution in water), a single peak is detected by UV or by using a beta detector.

The specific activity determined by mass spectrometry is about 300 GBq/mmol (8.0 Ci/mmole).

The total activity obtained, measured by liquid scintillator counting is 4.3 mCi.

Fixation Characteristics of the Compound of Example 1 on Soluble cRABP

The fixation of the compound of the present invention with cRABP has been characterized by saturation tests. The total fixation (nonspecific +specific) (curva a), is obtained by incubation of increasing concentrations (up to a maximum of 50 nM) of the compound of the present invention with a constant quantity (0.3 ml) of a homogenate of rat testicles (organ rich in cRABP). The nonspecific fixation of the tritiated compound is determined in parallel, by the measurement of the fixation with increasing concentrations of the radioactive ligand in the presence of a large excess (1 $\mu$M) of retinoic acid (curve c). An incubation time for 2 hours is necessary for the establishment of equilibrium conditions.

Once equilibrium is reached, the cRABP-tritiated ligand complex is separated from the nonlinked ligand by filtration on an exclusion gel Sephadex G25 column (Bio-Rad econo columns, 0.5×20 cm): the complex is eluted (elution peak at 2.5 ml), while the nonlinked ligand is retained in total on the column. A total separation is thus effected between the linked and nonlinked product. The eluation is made directly in the scintillation tubes and the radioactivity is measured by counting.

The results thus obtained are analyzed by nonlinear regression using as a model the Clark equation: (A. J. Clark, The Mode of Action of Drugs on Cells; A. Arnold and Co., London, 1933).

On FIG. 1, there is represented, on the abscissa, the initial concentrations of the ligand being studied, and on the ordinate, the concentrations at equilibrium of the ligand-receptor complex.

The difference between curves a (total fixation) and c (nonspecific fixation) gives the curve of specific fixation, curve b. The analysis of this curve provides the dissociation constant at equilibrium, (Kd), which is the concentration of product necessary for 50% saturation of the soluble receptor. This constant is a measure of the affinity of the ligand for its receptor, Kd being inversely proportional to affinity, (the weaker Kd is, the greater is the affinity). The total fixation curve a is analyzed in the same manner, after introduction of a linear component (nonspecific fixation) to the repression model; the resulting specific fixation curve in this manner (curve b) is in perfect accord with that obtained by difference.

This analysis gives a Kd value of 2.7±0.5 nM. The specific fixation is saturable and reversible. The nonspecific fixation is linear and nonsaturable in the concentration range employed, and represents less than 10% of the total fixation. Under the same conditions, the Kd value of retinoic acid is 2±0.8 nM, the nonspecific fixation representing approximately 25% of the total fixation.

Comparison with Tritiated Retinoic Acid

FIGS. 2 to 7 correspond to the competition tests and show the similarity of the fixation characteristics of retinoic acid, and the compound of Example 1.

These competition tests are carried out in the following manner: a fixed amount of the radioactive ligand (corresponding essentially to the half-saturation of the fixed amount of receptor which will be employed), is mixed with increasing quantities of cold ligand (non-radioactive). The receptor is then added and there is determined the amount of radioactive ligand fixed at equilibrium (in % of initial fixation in the absence of cold ligand, for the amount of receptor considered).

Figure 2:
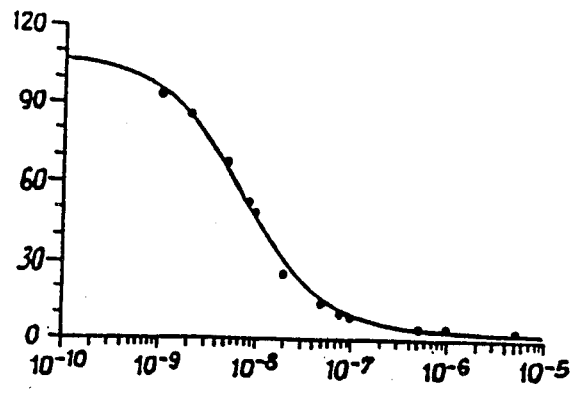
Figure 3:
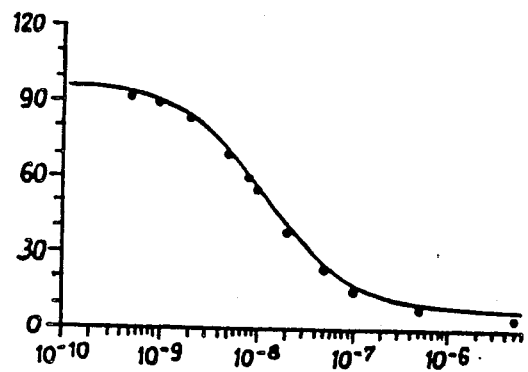
Figure 4:
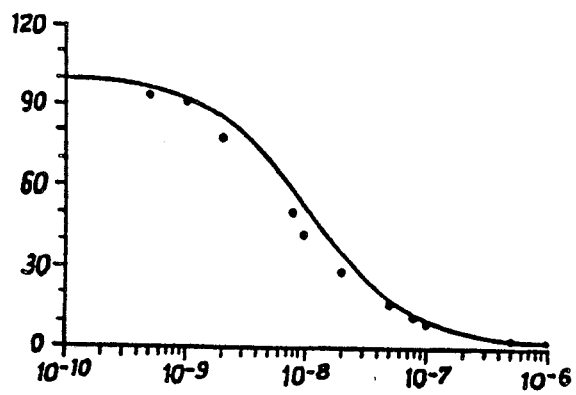
Figure 5:
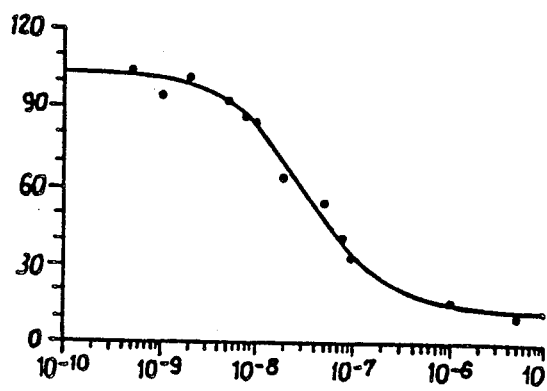

In FIGS. 2 to 7, there are indicated, on the abscissae, the increasing concentrations of cold ligand studied (in moles/liter), and, on the ordinates, the fixation of the radioactive ligand (in % of the maximum). The ligands studied are the following:

| FIG. 2: | radioactive ligand: compound of Example 1<br>cold ligand: retinoic acid |
|---|---|
| FIG. 3: | radioactive ligand: tritiated retinoic acid<br>cold ligand: The same as for FIG. 2. |
| FIG. 4: | radioactive ligand: tritiated compound of Example 1<br>cold ligand: The same but nonmarked compound (compound A). |
| FIG. 5: | radioactive ligand: tritiated retinoic acid<br>cold ligand: The same as for FIG. 4. |
| FIG. 6: | radioactive ligand: compound of Example 1<br>cold ligand: p-[(E)-2-(5,6,7,8-tetrahydro-5,5,8,8 -tetramethyl-2-naphthyl-propenyl]-benzoic acid, (Hoffman-La Roche), hereinafter called compound B. |
| FIG. 7: | radioactive ligand: tritiated retinoic acid<br>cold ligand: the same as for FIG. 6. |

Starting from the competition curves of FIGS. 2 to 7, there is determined in each case the IC$_{50}$ (concentration of cold ligand reducing the attachment of 50% of the tritiated ligand). This IC$_{50}$ value permits the calculation in each case of the dissociation constant at equilibrium (Kd) for the cold ligand.

The following values have been found:
FIG. 2: Kd = 4 nM ±19%
FIG. 3: Kd = 4 nM ±44%
FIG. 4: Kd = 6 nM ±30%
FIG. 5: Kd = 6 nM ±19%
FIG. 6: Kd = 16 nM ±58%
FIG. 7: Kd = 20 nM ±24%.

FIGS. 2 and 3 show the competition curves of cold retinoic acid with the compound of Example 1 (FIG. 2) and with tritiated retinoic acid (FIG. 3). The dissociation constants calculated in both cases are the same which suggests that the two radioactive ligands have similar fixation specificities.

In the same manner, it can be seen (FIGS. 4 and 5) that the Kd values obtained for compound A, by using both marked ligands, are the same.

Figure 6:
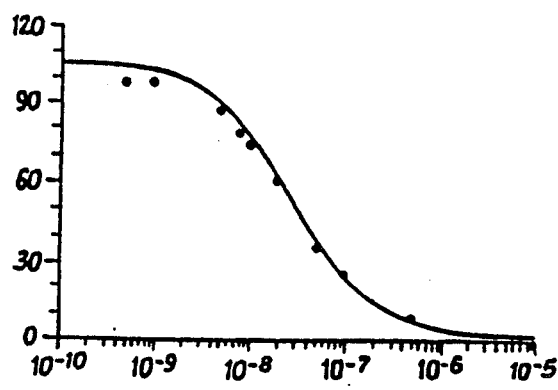
Figure 7:
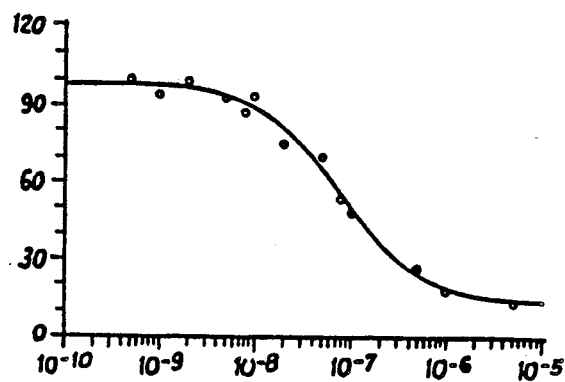

That is also verified in the case of compound B (FIGS. 6 and 7).

In conclusion, in all cases studied above, the calculated Kd's are independent of the tritiated ligand employed, which shows that these ligands are linked to the same receptor with similar specificities and that one can replace one by the other for the determination of the fixation of the retinoids on cRABP.

What is claimed is:

1. Tritium labelled 2-(5,6,7,8-tetrahydro-5,5,8,8-tetramethyl-2-naphthyl)-6-benzo [b] thiophene carboxylic acid.

2. The acid of claim 1 labelled in position 3 of the tetrahydronapthalene group.

3. The acid of claim 1 having a specific activity of at least 75 GBq/mmole.

4. In a method for determining the affinity of, the presence of, or the amount of, retinoids having a carboxylic group and/or in a method for the characterization of antibodies directed against 2-(5,6,7,8-tetrahydro-5,5,8,8-tetramethyl-2-naphthyl)-6-benzo [b] thiophene carboxylic acid and/or in a method for the quantification of the cRABP receptor of said retinoids, the improvement comprising using, as a radioactive marker, tritiated 2-(5,6,7,8-tetrahydro-5,5,8,8-tetramethyl-2-naphthyl)-6-benzo [b] thiophene carboxylic acid.

* * * * *